United States Patent [19]

Dunlop

[11] Patent Number: 5,509,428

[45] Date of Patent: Apr. 23, 1996

[54] METHOD AND APPARATUS FOR THE CREATION OF TRICUSPID REGURGITATION

[76] Inventor: Richard W. Dunlop, 14 Landing Rd., Kingston, Mass. 02364

[21] Appl. No.: 251,109

[22] Filed: May 31, 1994

[51] Int. Cl.$^6$ ................................................ A61B 19/00
[52] U.S. Cl. ........................................................... 128/898
[58] Field of Search ........................... 128/897, 898, 128/642; 600/15; 604/264, 280; 606/191, 192, 194, 200; 607/119, 122, 123, 126

[56] References Cited

U.S. PATENT DOCUMENTS

| | | | |
|---|---|---|---|
| 4,848,342 | 7/1989 | Kaltenbach | 606/194 |
| 4,861,330 | 8/1989 | Voss | 606/194 |
| 4,921,484 | 5/1990 | Hillstead | 606/194 |
| 5,235,977 | 8/1993 | Hirschberg et al. | 607/123 |

*Primary Examiner*—Angela D. Sykes
*Assistant Examiner*—Samuel Gilbert
*Attorney, Agent, or Firm*—John P. McGonagle

[57] ABSTRACT

A method and apparatus for the controlled inducement of tricuspid regurgitation for the purpose of treating congestive heart failure. The apparatus is comprised of a catheter onto which is affixed an expandable device. The catheter is percutaneously inserted into the patient's body, then moved within the central venous system until the end of the catheter traverses the tricuspid valve of the heart. The expandable device on the distal end of the catheter is then radially expanded to hold open the leaflets of the tricuspid valve. Tricuspid regurgitation, the backflow of blood from the right ventricle to the right atrium, then occurs. The intention of causing the regurgitation is to lower the pulmonary arterial pressure elevated as a result of congestive heart failure. Through careful monitoring of the patient's pulmonary arterial pressures and cardiac output, the degree of tricuspid regurgitation can be adjusted. The controls for the expansion of the catheter are outside of the body and in reach of the skilled physician.

4 Claims, 4 Drawing Sheets

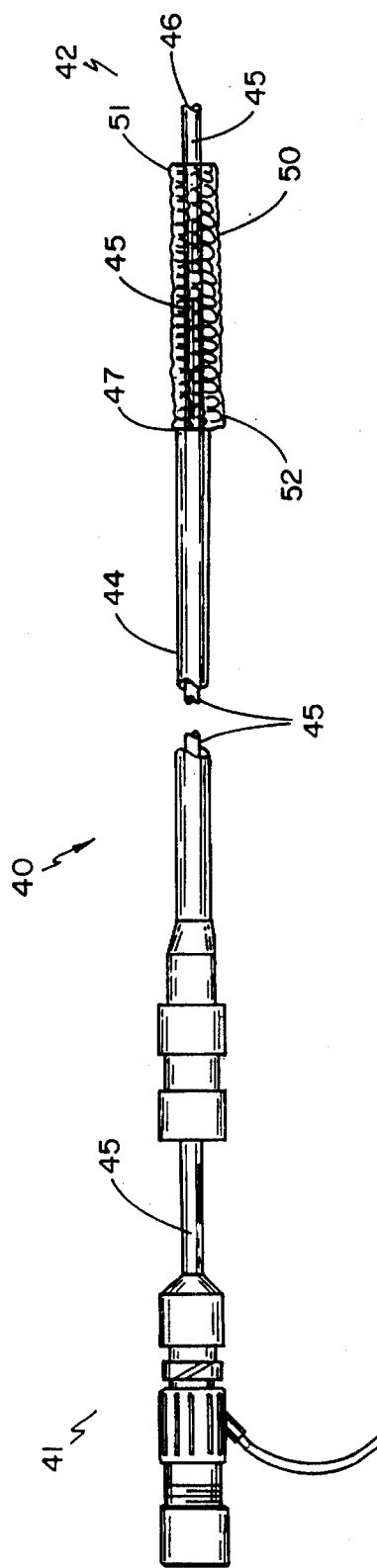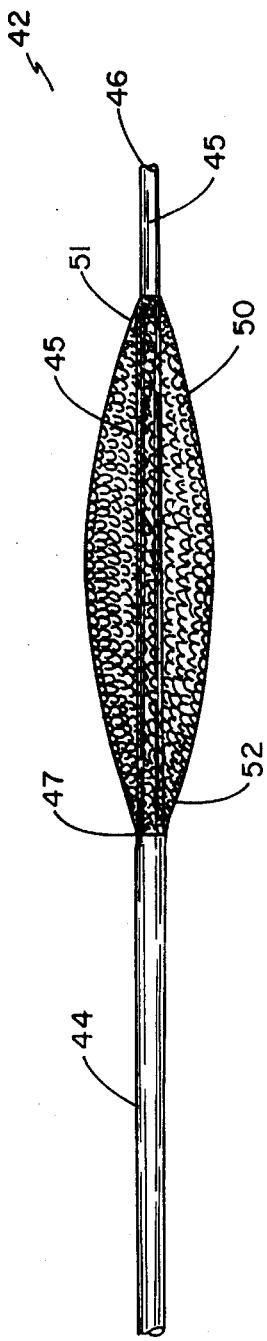
FIG. 3A
FIG. 3B

METHOD AND APPARATUS FOR THE CREATION OF TRICUSPID REGURGITATION

BACKGROUND OF THE INVENTION

The present invention relates to a method and catheter to be used in the creation of tricuspid regurgitation for the treatment of congestive heart failure.

Congestive Heart Failure (CHF) is a condition characterized by the inability of the heart to pump blood at a rate needed to maintain adequate blood flow throughout the body. CHF most commonly occurs as a result of ischemic heart disease, myocardial infarction, cardiomyopathy, or valvular disorders. In these conditions, the left ventricle (which pumps oxygenated blood to the body) can fail, while the right ventricle (which pumps deoxygenated blood to the lungs) continues to function normally. When this occurs, the pulmonary arterial pressures increase and fluid begins to exude from the pulmonary capillaries into the pulmonary interstitium and eventually into the alveoli, the tiny air sacs where gas exchange takes place. Fluid in the alveoli impedes gas exchange across the alveolar membranes, which then lowers the blood oxygenation. The resulting hypoxemia has a detrimental effect on the cardiac muscle, which requires large amounts of oxygenated blood to function normally, and results in an even more profound heart failure. This cycle, if left untreated, continues until the patient succumbs, in effect, drowning in his own pulmonary fluids.

Conventional therapies for CHF act by reducing pulmonary arterial pressures, and consist of drugs which either: (1) reduce overall blood volume, or "pre-load reducers" ( i.e., diuretics); (2) reduce systemic capillary resistance, or "afterload reducers" (i.e., vasodilators); or (3) enhance cardiac function, or "inotropic" agents (i.e., digitalis). These conventional therapies are usually very effective in the treatment of CHF, and their benefits often quite dramatic. Occasionally, however, a patient may develop CHF that is refractory to all conventional treatments. These patients are in danger of succumbing to the effects of hypoxemia unless some other treatment is begun which can break the heart failure—pulmonary edema cycle. For these patients, the instant invention offers an alternative therapy.

The concept for this catheter came from the knowledge that some patients with CHF who develop tricuspid regurgitation in the course of their disease may actually experience improvement in their pulmonary symptoms.

The tricuspid valve is a one-way valve located between the right atrium and right ventricle, and regulates blood flow between the two cavities. When the ventricles dilate during diastole, the tricuspid valve opens to allow deoxygenated blood to flow from the right atrium to the right ventricle. When the ventricles contract during systole, the tricuspid valve closes to prevent blood from refluxing back into the right atrium. Simultaneously, the pulmonary valve opens, and the deoxygenated blood is ejected from the right ventricle into the pulmonary arteries enroute to the lungs.

Tricuspid regurgitation, a condition whereby a faulty valve allows blood to reflux backward through the valve into the right atrium, can sometimes occur naturally in the course of congestive heart failure. It has been found that some patients who develop tricuspid regurgitation during the course of CHF actually experience improvements in their pulmonary symptoms. One might then ask whether patients with CHF who are refractory to conventional treatments might benefit from the creation of a reversible and controllable tricuspid regurgitation. The instant invention discloses catheter apparatus and a method for controllably inducing tricuspid regurgitation in those patients.

There are many devices disclosed in the prior art which have been developed for use on patients with cardiac problems. U.S. Pat. No. 4,861,330 (Voss) discloses a cardiac assist device comprised of an inflatable balloon that is inserted into a collapsed ventricle of the heart. The balloon is inserted into the ventricle through a coronary valve by means of a catheter, radiopaque dye and skilled surgery. The tip of the balloon houses a needle that holds the balloon in place. Inflation and deflation of the balloon is controlled from outside the body and is synchronized with the beating of the cavity housing the device. As a result, the cavity is assisted in expanding, contracting, and in pumping blood. The assistance is two fold in both the radial pressure the balloon puts on the ventricle walls and the added mass of the balloon within the ventricle increasing the internal pressure and therefore outflow of blood.

U.S. Pat. No. 5,034,001 (Garrison et al.) discloses a device and method for repairing a damaged blood vessel. The device comprises a catheter with a mesh-like shell about a center bar that is radially expandable and contractible. The mesh is hollow so as to allow the free flow of blood within it. The device is navigated into the damaged blood vessel by conventional surgical means. Once within the damaged area, the mesh, through externally controlled means, is radially expanded to the diameter of the damaged vessel to absorb the vessel pressure. The spacing of the mesh fibers are such that any flaps (loose hanging pieces of the vessel wall that may fall down into the vessel cavity thus blocking the flow of blood) are held in place and allowed to heal. This device is generally, although not limited to use within arteries.

U.S. Pat. No. 4,781,682 (Patel) discloses a device and method for inserting a catheter into an artery or the like. The device includes a guiding hollow catheter housing a dilating catheter therein. The guiding catheter deposits the dilating catheter into the narrowing of an artery for the performance of coronary angiography and angioplasty. The device further includes outer flaps mounted on an outer tube which when extended, from controls outside the body, serve as a mount to secure in place the dilating catheter.

U.S. Pat. No. 4,834,724 (Geiss et al.) discloses a device for aspirating fluids from a body cavity or hollow organ such as the stomach. The device comprises two lumens, one acting as a sump for the other. The device has a helical end for aligning the intake end with the lining of the stomach. The end also has ports facing in all directions so as to prevent the drawing in of stomach lining thus preventing the creation of an ulcer and internal piercing.

U.S. Pat. No. 3,828,767 (Spiroff) discloses a catheter with a tip comprising axial spaced holes of different diameters. The hole arrangement provides for the controlled ejection of fluid from a catheter end without the uncontrolled whipping associated with pressure build up within the catheter end. The result includes an end to the uncontrolled whipping about of the catheter tip and damage caused thereby.

U.S. Pat. No. 5,076,285 (Hess et al.) discloses a medical electrode lead comprising a helical extension from the distal end for screwing into heart tissue thereby mounting the device within the heart.

U.S. Pat. No. 4,952,215 (Ouriel et al.) discloses a volvultome for opening the valves of the veins in the event of failure. The disruption occurs as a result of disrupting heads mounted on the end of a rigid support. The device is inserted through an incision and is lead along the vein to the problem valve.

U.S. Pat. Des. Nos. 33,246 (Pumphrey) and 59,952 (Bruen) disclose designs for syringe nozzles. U.S. Pat. De. No. 33,456 (Harris) discloses a design for a catheter.

U.S. Pat. No. 5,106,381 (Chikama) discloses a bending device for use with an endoscope, catheter or the like, comprised of a cylindrical frame housing therein, annular portions, and openings within said annular portions, divided by resilient thin plates for the flow of blood therein. The device further comprises wires for bending the frame and thin plates.

U.S. Pat. No. 3,592,184 (Watkins) discloses a device and method for siphoning and replacing blood. The device comprises a catheter inserted into the aorta, a membrane expanded radially to set the catheter centrally within the hollow of the aorta, two end placed ports for the intake and outtake of blood and means to connect the catheter to a blood pump.

U.S. Pat. No. 5,041,084 (Devires et al.) discloses a single stage catheter inserted into the right atrium through the superior vena cava. The catheter is used during open heart surgery to bypass the flow of oxygen poor blood away from the heart and into a life support unit. The catheter further includes several openings positioned to fall within the right atrium as well as a spiral lead flute for insertion into the inferior vena cava.

U.S. Pat. Des. No. 196,998 (Glassman) discloses a design patent for a common bile duct probe. In addition, Glassman, in U.S. Pat. No. 4,299,225, discloses a device for removal of gall stones from the common bile duct. The device comprises a catching basket securely fastened between two catheter ends that allow the device to be easily inserted through an incision and freely moved along the bile duct. During movement, the dislodging basket can be contracted and expanded as needed.

U.S. Pat. No. 4,927,426 (Dretler) discloses a catheter device for capturing, disintegrating and then discharging the remains of kidney stones and the like. A capturing head, housed within the catheter, is extended to capture a kidney stone, and then is retracted into the catheter with the stone lodged therein. A laser is used to disintegrate the stone and the capturing head is then extended outside the catheter body wherein the disintegrated remains of the kidney stone are released.

However, none of the many devices disclosed in the prior art which have been developed for use on patients with cardiac problems address the problem of creating a tricuspid regurgitation.

SUMMARY OF THE INVENTION

In view of the foregoing disadvantages inherent in the known methods and apparatus now present in the prior art, the present invention provides an apparatus and method for creating a reversible and controllable tricuspid regurgitation, and maintaining that regurgitation long enough to allow the heart to recover from the insult which led to the heart failure. During the time that the apparatus would be in place, the patient's pulmonary arterial pressures and cardiac output would be closely monitored, and any adjustments in the degree of regurgitation made accordingly. A preferred embodiment of the apparatus of the invention comprises a catheter, the distal end of which accommodates an expandable device. The device may comprise: an expandable metal or synthetic cage or basket; an irregularly shaped balloon; or a metal or plastic wire which assumes a coiled shape when extended from the end of the catheter. The method for using the device comprises percutaneously inserting the catheter into the subclavian or femoral vein, and advancing the catheter into the heart area so as to position the expandable portion of the catheter across the tricuspid valve. This portion of the catheter is then expanded to hold the leaflets of the tricuspid valve open, thereby inducing regurgitation. The degree to which the valve is held open is controlled from outside the body, during which time the patient's pulmonary condition is closely monitored.

These together with other objects of the invention, along with various features of novelty which characterize the invention, are pointed out with particularity in the claims annexed hereto and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

FIG. 3A is a view of a catheter, the distal end of which contains an expandable cage or basket, in its unexpanded mode.

FIG. 3B is a close-up view of the distal end of the catheter of FIG. 3A, expanded.

DETAILED DESCRIPTION OF INVENTION

Figure 1:
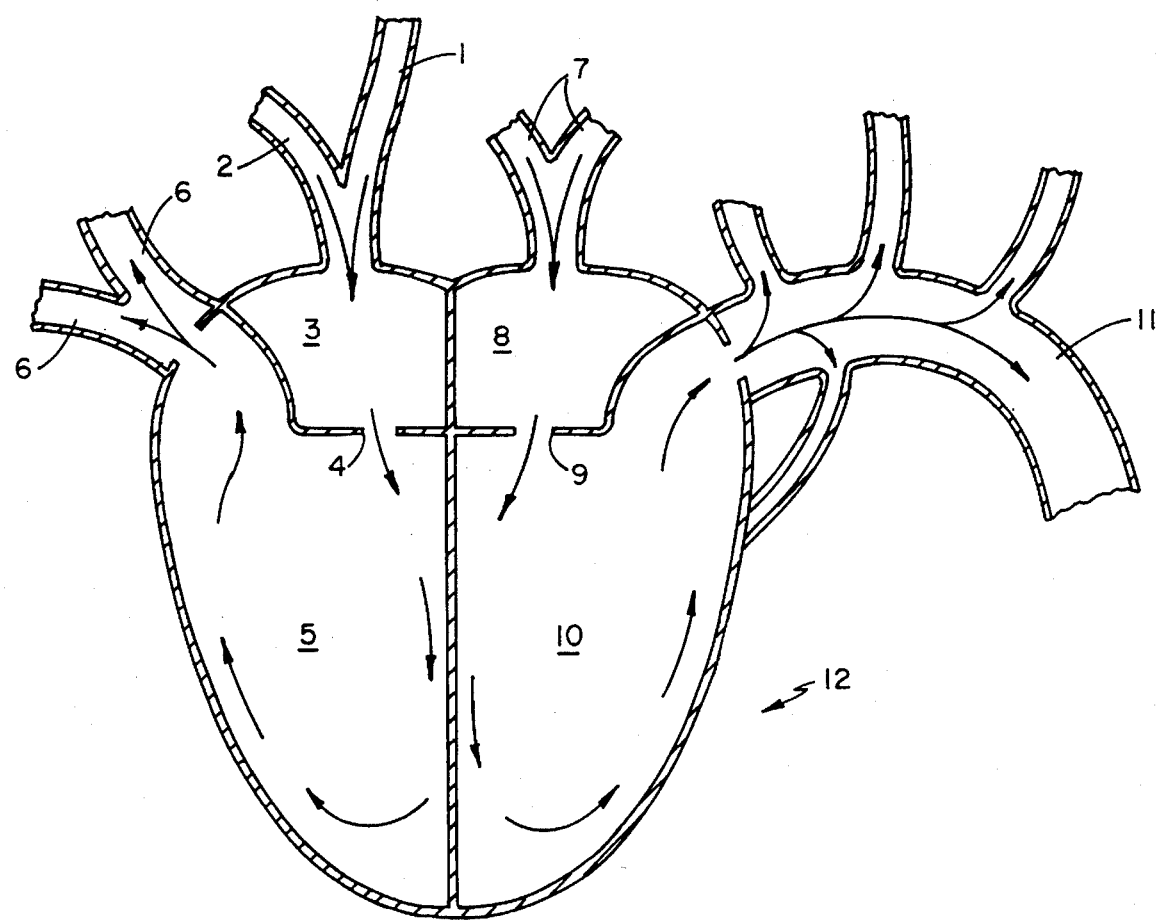
FIG. 1 is a schematic diagram of the heart showing cardiac blood flow.
Figure 2:
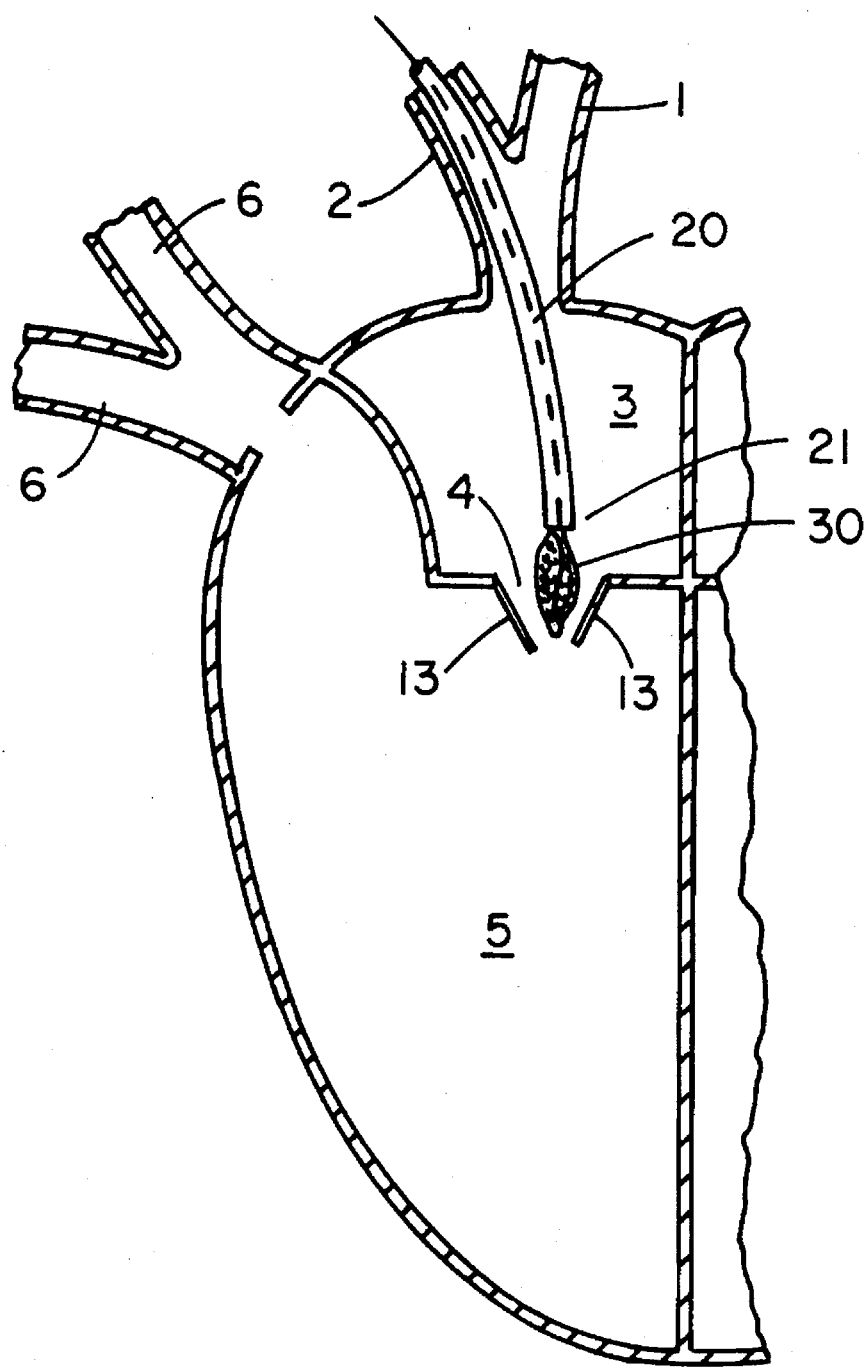
FIG. 2 is a schematic representation of the right atrium and right ventricle with the catheter therein.
Figure 4:
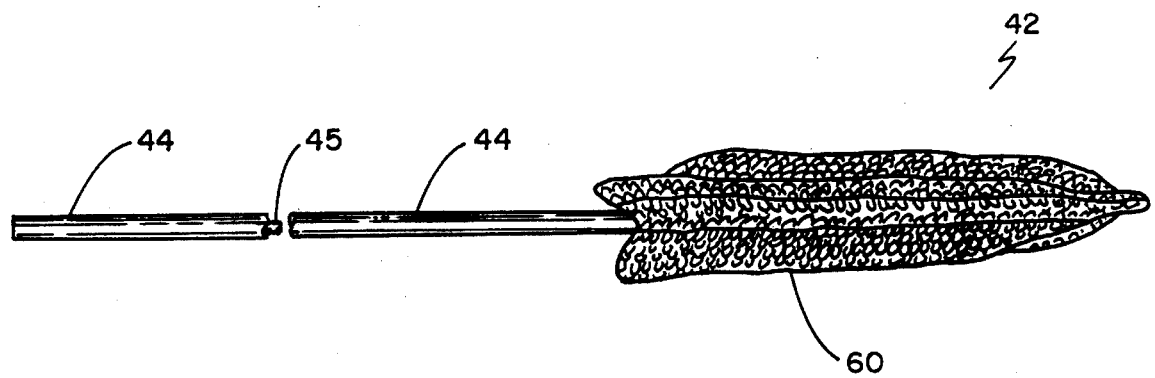
FIG. 4 is a view of a catheter, to the distal end of which is affixed an irregularly shaped inflatable balloon.
Figure 5:
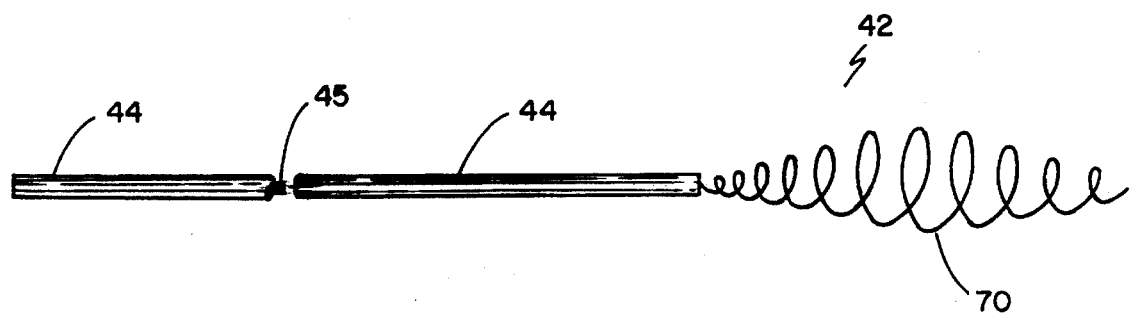
FIG. 5 is a view of a catheter housing an expandable coil.

Referring to the drawings in detail wherein like elements are indicated by like numerals, there is shown in FIG. 1 a schematic depiction of cardiac hemodynamics, in FIGS. 2–3 an embodiment of the invention 1 incorporating the method and apparatus of the present invention. Alternate apparatus embodiments are shown in FIGS. 4 and 5.

Cardiac blood flow may be said to begin at the juncture of the superior and inferior venae cavae, 1 and 2, respectively, where all oxygen-depleted blood in the body is forced into the right atrium 3. The natural pumping action of the heart 12 draws the blood through the tricuspid (atrioventricular) valve 4 into the right ventricle 5. The right ventricle 5 then drives the blood to the lungs via the pulmonary arteries 6. Oxygenated blood returns from the lungs to the heart by way of pulmonary veins 7 which lead into the left atrium 8, passing then through mitral (bicuspid) valve 9 into the left ventricle 10. Contraction of the left ventricle 10 forces the blood into the aorta 11 which then distributes the blood throughout the body.

The instant invention comprises the method and apparatus for the controlled inducement of tricuspid regurgitation for the purpose of treating congestive heart failure. The apparatus is comprised of a catheter 20 onto which is affixed an expandable device 30. Referring especially to FIG. 2, the catheter 20 is percutaneously inserted into the patient's body, then moved within the central venous system 2 or 1 and through the right atrium 3 until the end of the catheter 20 traverses the tricuspid valve 4 of the heart 12. The expandable device 30 on the distal end 21 of the catheter 20 is then radially expanded to hold open the leaflets 13 of the tricuspid valve 4. Tricuspid regurgitation, the backflow of blood from the right ventricle 5 to the right atrium 3, then occurs. The intention of causing the regurgitation is to lower the pulmonary arterial pressure elevated as a result of congestive heart failure. Through careful monitoring of the patient's pulmonary arterial pressures and cardiac output, the degree of tricuspid regurgitation can be adjusted. The controls for the expansion of the catheter are outside of the body and in reach of the skilled physician.

The method for the controlled inducement of tricuspid regurgitation using a catheter 20 comprises the steps of: percutaneous insertion of the catheter into the central venous system (subclavian or femoral vein); under fluoroscopic observation advancing the catheter 20 to a point where the expandable distal end 30 of the catheter is across the tricuspid valve 4; radially expanding said expandable end 30 by external means, thereby holding open the leaflets 13 of the tricuspid valve 4 and causing tricuspid regurgitation; closely monitoring the patient's pulmonary arterial pressures and cardiac output; and adjusting the degree of tricuspid regurgitation accordingly.

FIGS. 3A and 3B discloses a specific example of the apparatus of the present invention. The apparatus disclosed is a hollow catheter 40 having a proximal end 41 and a distal end 42. The catheter 40 is comprised generally of an flexible outer housing 44 with a nylon cannula 45 concentrically positioned within and along the length of said housing 44 and protruding past the distal end 47 of said housing 44. A guide wire 46 is concentrically positioned within and along the length of said cannula 45. Affixed to said catheter distal end 42 is an expandable mesh cage 50. FIG. 3A shows the mesh cage 50 in its closed, unexpanded mode and FIG. 3B shows the mesh cage 50 in its expanded mode. Said mesh cage 50 can be made of metal or plastic or other synthetic material. The distal end 51 of the mesh cage 50 is attached to the cannula 45 protruding from the distal end 47 of the housing 44 while the proximal end 52 of the mesh cage 50 is affixed to the distal end 47 of said housing 44. Said cannula 45 can be controlled, by conventional means, from outside the body (not shown), by pulling or pushing, thereby causing the mesh cage 50 to expand or contract. The catheter 40 is percutaneously inserted into the patient's body, then moved within the central venous system 2 or 1 and through the right atrium 3 and is positioned so that the mesh cage 50 begins to traverse the tricuspid valve 4 of the heart 12. The mesh cage 50 is then radially expanded to hold open the leaflets 13 of the tricuspid valve 4.

FIG. 4 discloses another embodiment of the catheter expandable device 30 wherein the mesh cage 50 of FIGS. 3A and 3B is replaced with an inflatable irregularly shaped balloon 60 affixed to the catheter distal end 42. Said balloon 60 can assume any regular or irregular shape when inflated, provided it allows for blood to reflux back through it while the balloon holds the leaflets of the tricuspid valve open. Said balloon 60 can be made of non-thrombogenic material, is connected to a separate lumen within the catheter, and is expanded and contracted (inflated and deflated) through external means by methods known to one skilled in the art. U.S. Pat No. 4,861,330 discloses a catheter housing an expandable balloon for use within the heart and is incorporated herein by reference.

FIG. 5 discloses another embodiment of the catheter expandable device 30 wherein the mesh cage 50 of FIGS. 3A and 3B is replaced with an expandable coil 70. Housed within said catheter distal end 42 and shown in its expanded mode is an expandable coil 70. Said expandable coil 70 is attached to an inner rod 45, forming a second cannula which can be retracted within the catheter distal end 42, or can be expanded into a coiled position, i.e., lenticular shape, when extended from the end of catheter end 42. The coil is controlled from outside the body through means known to one skilled in the art.

It is understood that the above-described embodiments are merely illustrative of the application. Other embodiments may be readily devised by those skilled in the art which will embody the principles of the invention and fall within the spirit and scope thereof.

What is claimed is:

1. A method of treating a patient's congestive heart failure, a condition resulting in elevation of the pulmonary arterial pressures, comprising:

selecting a catheter comprising an elongated hollow body onto which or through which is affixed a radially expandable device which can be controlled from outside the patient's body;

inserting the catheter into a patient's venous system;

advancing the catheter through the patient's venous system into a patient's heart area so as to position the radially expandable device of the catheter across a tricuspid valve;

radially expanding the radially expandable device of the catheter, through manipulation of controls located outside the patient's body, so that the catheter holds open leaflets of the tricuspid valve;

inducing tricuspid regurgitation by the holding open of said leaflets of the tricuspid valve;

monitoring the patient's pulmonary pressures and cardiac output;

adjusting, as desired, the degree of tricuspid regurgitation to affect improvement in a patient's condition; and removing the catheter from the patient's body.

2. The method according to claim 1, wherein:

the step of radially expanding the radially expandable device of the catheter comprises expanding an expandable mesh cage.

3. The method according to claim 1, wherein:

the step of radially expanding the radially expandable device of the catheter comprises expanding an inflatable irregularly shaped balloon, which, when inflated, is adapted to allow blood to reflux back past the balloon while the balloon holds open the leaflets of the tricuspid valve.

4. The method according to claim 1, wherein:

the step of radially expanding the radially expandable device comprises expanding an expandable coil.

\* \* \* \* \*